United States Patent [19]

Fixel

[11] Patent Number: 4,657,001

[45] Date of Patent: * Apr. 14, 1987

[54] ANTIROTATIONAL HIP SCREW

[76] Inventor: Irving E. Fixel, 111 N. 31st Ave., Hollywood, Fla. 33021

[*] Notice: The portion of the term of this patent subsequent to Feb. 21, 2001 has been disclaimed.

[21] Appl. No.: 634,205

[22] Filed: Jul. 25, 1984

[51] Int. Cl.$^4$ .............................................. A61F 5/04
[52] U.S. Cl. ............................ 128/92 YS; 128/92 YT
[58] Field of Search ......... 128/92 BB, 92 BA, 92 BC, 128/92 B, 92 C, 92 CA

[56] References Cited

U.S. PATENT DOCUMENTS

| | | | |
|---|---|---|---|
| 2,267,925 | 12/1941 | Johnston | 128/92 BB |
| 2,327,434 | 8/1943 | Johnston | 128/92 BA |
| 2,702,543 | 2/1955 | Pugh et al. | 128/92 BB |
| 3,002,514 | 10/1961 | Deyerle | 128/92 BA |
| 3,374,786 | 3/1968 | Callender, Jr. | 128/92 R |
| 3,530,854 | 9/1970 | Kearney | 128/92 BA |
| 3,892,233 | 7/1975 | Vestby | 128/92 BA |
| 4,432,358 | 2/1984 | Fixel | 128/92 BB |
| 4,441,492 | 4/1984 | Rydell et al. | 128/92 BA |
| 4,530,355 | 7/1985 | Griggs | 128/92 B |

OTHER PUBLICATIONS

*Machinery's Handbook*, 20th ed. 1978, pp. 1274–1277, a portion of "Screw Thread Systems".
"Richard's Offers the Solution", brochure by Richards Manufacturing Co. Inc., 1450 Brooks Rd., Memphis, Tenn. 38116.
"Biomet Concentric Hex", brochure by Biomet Inc., P.O. Box 587, Warsaw, Ind. 46580.
"Wright Hip Compression Screw/Plate", by Wright, P.O. Box 100, Arlington, Tenn. 38002.

*Primary Examiner*—Gene Mancene
*Assistant Examiner*—C. W. Shedd
*Attorney, Agent, or Firm*—Richard M. Saccocio

[57] ABSTRACT

An implantable compression hip screw is disclosed. A unique antirotational/locking device used in combination with axially aligned grooves in a barrel plate and a lag screw prevents the fractured portion of the femur from rotating during the postoperative period. The antirotational/locking device comprises elongated rods which fit within the aligned grooves and thereby allow sliding of the lag screw relative to the barrel plate during the postoperative period.

4 Claims, 7 Drawing Figures

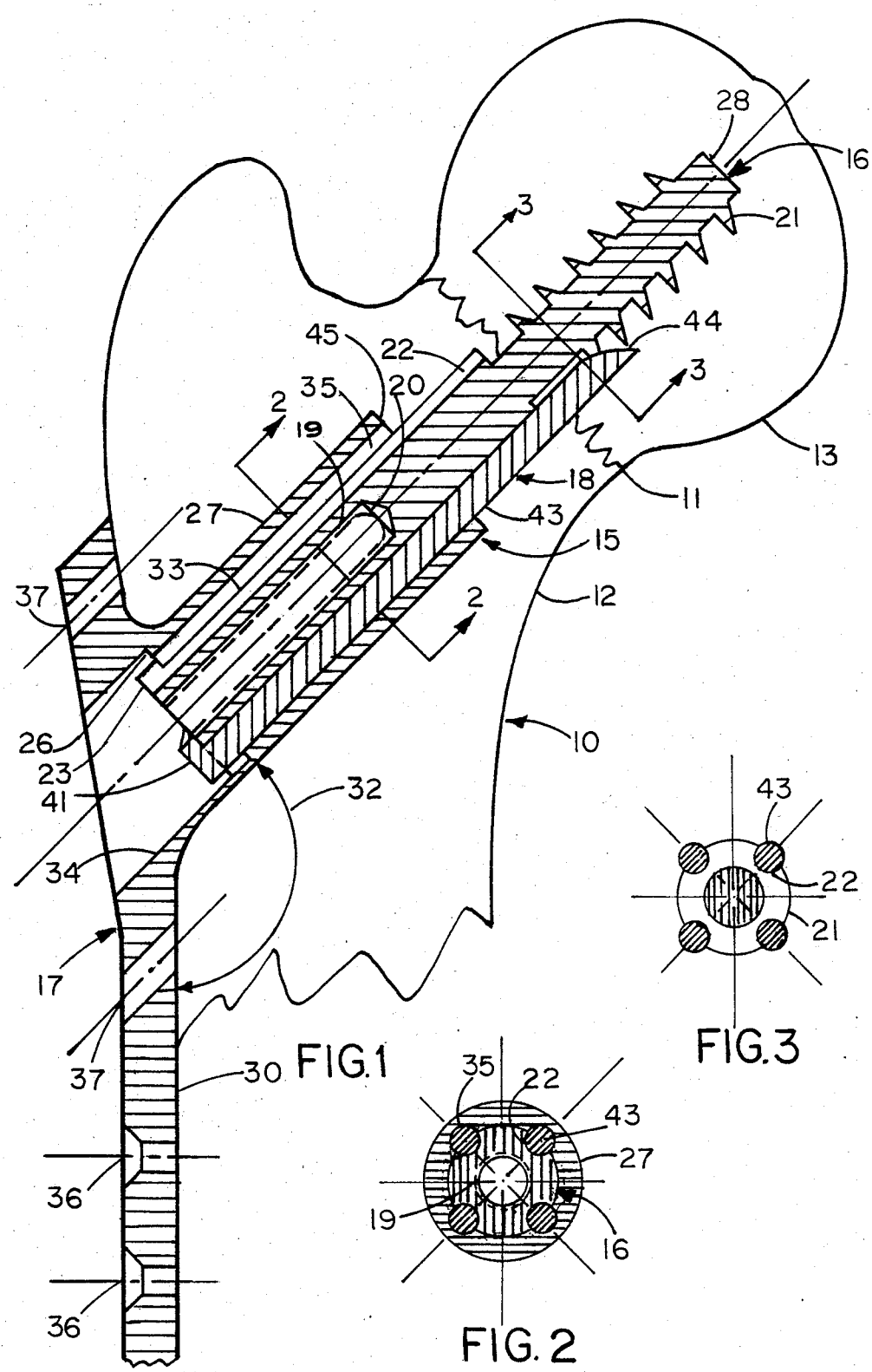

4,657,001

ANTIROTATIONAL HIP SCREW

BACKGROUND OF THE INVENTION

1. Field of the Invention

This invention relates in general to the field of implanted bone fixation devices and in particular to a hip screw for operative reduction and internal fixation of femoral head, neck or intertrochanteric fractures which allows relative sliding of the device and yet prevents rotation of the broken portion of the bone following surgery.

2. Description of the Prior Art

In one of my prior patents, specifically U.S. Pat. No. 4,432,358, Compression Hip Screw Apparatus, issued Feb. 21, 1984, I described the problems associated with hip screws which were designed for use with certain types of fractures of the upper femur such as the head, neck or intertrochanter fractures. In general, these problems involve prevention of the femoral head from rotating relative to the femur during the postoperative period and allowing further impaction of the broken bone portions during the postoperative period.

As explained in the referenced patent, it is highly desirable to "key" the lag screw to the barrel plate in order to prevent femoral head rotation relative to the femur during the postoperative period when the hip joint is being normally used such as when walking, going up stairs, and other like body motions. Any tendency for the head to rotate relative to the femur must be resisted by the union formed between the broken bone and the implanted compression hip screw. Without support from the compression hip screw, there is the distinct possibility of failure of the fragile union of the fracture during the postoperative period. The key-keyway feature of certain compression hip screws served to prevent such rotation. Since the femoral head is attached to the lag screw and the femur is attached to the barrel plate, keying the lag screw to the barrel plate in effect keys the head to the femur. Unfortunately, the key-keyway devices created other problems which make their use less desirable. Friction between the key-keyway prevents relative motion between the lag screw and the barrel plate and thereby tends to prevent additional impaction of the fusioned bone fragments following surgery. Postoperative impaction is highly desirable. Since the key-keyway requires fairly close mechanical tolerances between the fitting parts, the fitup between the lag screw and the barrel during surgery is quite difficult. Any slight misalignment resulting from the preliminary hole drilling operations causes improper alignment of the shaft of the barrel plate relative to the shaft of the femur as well as improper alignment between the axial centerline of the lag screw and the centerline of the barrel. Any such misalignment results in bending movement and stresses being induced in the lag screw and the barrel plate. Ultimately, however, these stresses and bending loads are transmitted to the femur and the unionized fracture, which is obviously undesirable, and may lead to failure of the unionized fracture.

A number of attempts to minimize the adverse effects of the key-keyway design have in the most part proved relatively unsuccessful. Shortening of the key tends to reduce binding caused by friction, but does not eliminate the tendency to bind. Extensions added to the distal end of the lag screw allows the operating surgeon to "find" the lag screw during placement of the barrel plate but the added parts increase the overall stackup of tolerances increasing the possibility of axial misalignment between the screw and barrel which tends to increase the resulting bending movements and loads which must be carried by the fusioned bone fragments. Thus, the key-keyway design of compression hip screw has not provided the answer to the problem of prevention of femoral head rotation. As a result, and obviously a compromise, there has been a recent tendency for surgeons to return to the original keyless design which, of course, does not address the head rotation problem but does allow for low friction sliding during the postoperative period.

My prior referenced patent, disclosed a new and different compression hip screw which does overcome the abovestated problems. A unique locking assembly is used to frictionally lock the lag screw, the compression nut and the barrel of the hip plate. While shown to be effective, there still exists the need to provide new and improved compression hip screws which are simple in terms of surgical procedures, are effective in terms of impaction during and after surgery, and are effective to maintain fusion of the broken bones or fragments during the postoperative period when the device is being used. The present hip compression screws disclosed and claimed herein accomplish these objectives.

SUMMARY OF THE INVENTION

The inventive implant is adapted to be applied to a femur having one or more breaks across the proximal end thereof such as neck, head or intertrochanteric fractures.

In one embodiment, the barrel of a barrel plate and a lag screw are each provided with axially aligned grooves. The outer diameter of the lag screw is only slightly smaller than the inner diameter of the barrel to allow guidance and sliding. The lag screw shoulders against a bearing surface within the barrel to allow for impaction of the bone fragments by tightening of the lag screw. When the barrel plate and the lag screw are correctly positioned and fixed in place, an antirotational/locking pin assembly is inserted into the aligned grooves. A friction or force fit between the bone and the exposed ends of the pin assembly maintains a fixed position of the pin assembly. The pin assembly positively prevents the broken portion of the bone from rotating during the postoperative period when the patient is using his legs for purposes of locomotion, climbing, etc. The pin assembly also locks together the lag screw and the barrel plate. The grooved alignment between the lag screw and the barrel allows for impaction during the postoperative period.

BRIEF DESCRIPTION OF THE DRAWINGS

Various other objects, advantages and features of the invention will become apparent to those skilled in the art from the following discussion taken in conjunction with the following drawings, in which:

FIG. 1 is a partial, cross-sectional view of one embodiment of the present invention as applied to the proximal end of a femur having a fracture across the neck thereof, the locking pin assembly is partially shown for purposes of clarity;

FIG. 2 is a cross-sectional view taken along the line 2—2 of FIG. 1, with all of the pins of the locking pin assembly being shown;

FIG. 3 is a cross-sectional view taken along the line 3—3 of FIG. 1, with all of the pins of the locking pin assembly being shown;

DESCRIPTION OF THE PREFERRED EMBODIMENTS

Figure 4:
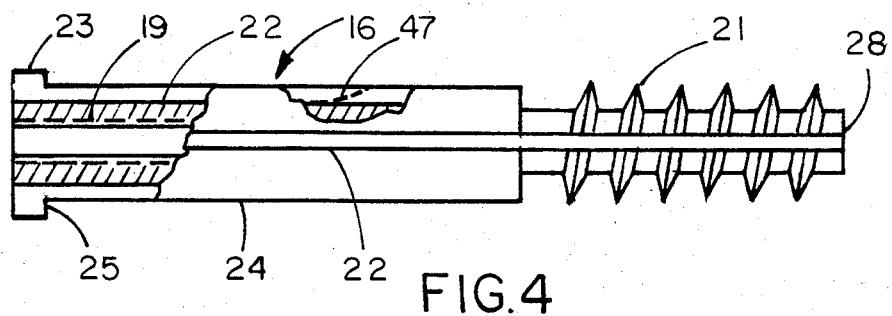
FIG. 4 is a side view of a lag screw, partially in cross section.

Referring now to the drawings where like characteristics and features among the various figures are denoted by like reference characters. The upper portion of the femur 10 is shown in FIG. 1. For purposes of illustration only, the fracture of femur 10 is shown to be across the neck 11 thereof. It is to be understood, however, that the inventive hip compression screw may be used with other femoral fractures such as head, intertrochanteric and subtrochanteric fractures. It is to be noted that any displacement of the femoral head relative to the femur prior to the surgery is reduced as much as possible prior to the application of the inventive as shown in FIG. 1.

In general, the inventive hip compression screw 15 comprises a lag screw 16, a barrel plate 17 and an antirotational/locking pin assembly 18. Lag screw 16 comprises an elongated bar having a generally circular cross section as shown in FIGS. 2 and 3. A blind tapped hole 19 is provided in one end of screw 16 for purposes of removal of screw 16 should it be necessary to do so. Hole 19 may be provided with left-handed threads to facilitate removal. An appropriate tool (not shown) may be inserted and threaded into hole 19 and when bottomed out at the blind surface 20 thereof, will then cause lag screw 16 to be rotated out of threaded engagement with femoral head 13. Threads 21 at the opposite end of lag screw 16 comprise right-handed threads.

FIG. 4 also shows lag screw 16 but separate and apart from the inventive compression hip screw 15. Grooves 22 are provided along the entire length of lag screw 16 including head portion 23. In the embodiment shown, four grooves 22 are provided, with each being spaced at 90° intervals around the circular periphery of the screw 16. As few as one groove 22 may be employed in the invention with good results, i.e., one groove in combination with one pin will prevent femoral head 13 rotation as will be more fully explained hereinafter. More grooves, however, are preferred. Grooves 22 may have a semicircular or rectangular cross-sectional shape. In the embodiment shown, the semicircular shape is utilized. Head portion 23 of lag screw 16 has a larger outer diameter than the shank portion 24 so as to provide a bearing surface 25 which bears against a corresponding mating surface 26 provided in barrel portion 27 of barrel plate 17 as shown in FIGS. 1 and 4. Threads 21 of lag screw 16 may comprise self-tapping lag screw threads having an outer diameter substantially equal to the outer diameter of the shank 24. Threads 21 may have a flat end 28 so as to allow all threads 21 to be used for engagement with the femoral head 13 and to prevent the possibility of penetrating through and out of femoral head 13. The length of threads 21 should be such that when lag screw 16 is fully seated within compression hip screw 15 and the broken portion of the bone is reduced or in firm contact with the nonbroken portion of femur 10, all of threads 21 are located within the broken portion, such as shown in FIG. 1.

The barrel plate 17 comprises an elongated plate portion 30 which is integrally connected to barrel portion 27. Barrel portion 27 extends away from plate portion 30 at an obtuse angle 32. Barrel portion 27 has a smooth bore 33 therethrough. A counterbore 34 is provided at the lateral end of bore 33 for purposes of providing the seat or bearing surface 26 for head 23 of screw 16 to bear against when screw 16 is tightened. Grooves 35 are provided within bore 33 in barrel portion 27. Grooves 35 in barrel 27 coincide with the location and the number of grooves 22 in screw 16. If semicircular grooves are used in screw 16. semicircular grooves in bore 33 would be rectangularly shaped. Again, one groove 35 may be satisfactorily employed but more are preferred. The plate portion 30 of barrel plate 17 comprises an elongated, flat plate adapted to fit against the lateral side of the femur 10. Holes 36 are provided through the plate portion for screws which allow for attachment to the femur 10, as is well known in the art. Only two holes 36 are shown for purposes of simplicity. Holes 37 in plate 30 allow for the insertion of pins (not shown) into the acetabulum which may be used during the surgery to negate the tendency of head 13 to rotate when lag screw 16 is inserted and tightened.

Pin antirotational/locking assembly 18 comprises a head 41 with a hole 42 therethrough and one or more extending elongated pins 43. In FIG. 1, only a portion of pin assembly 18 is shown for purposes of simplicity and clarification. The cross-sectional shape of pins 43 matches the combined shape of grooves 22 and 35. The circumferential location and number of pins 43 coincides with the location and number of grooves 22 and 35 in lag screw 16 and barrel 27, respectively. The length of pins 43 is substantially equal or slightly shorter than the length of lag screw 16. Pins 43 are firmly attached to head 41 such as by welding, or brazing or may be made integrally with head 41. The outer diameter of head 41 is substantially equal to the diameter of the circle circumscribed around the outside of pins 43 or slightly larger than the diameter of bore 33 in barrel 27.

The positions of barrel plate 17, lag screw 16 and pin locking assembly 18 shown in FIG. 1 represents their relative positions when an operating surgeon has reduced the fracture 11 thereby seating fractured head 13 firmly against the broken main portion 12 of the femur 10 and fully inserted and applied the compression hip screw 15 to complete the operation.

The following comprises a general description of a technique which may be used to insert and apply the inventive implant and to further describe the same.

When the hip fracture, which for discussion is assured to be a fracture of the femur across its neck, is well or sufficiently reduced, and the patient is properly prepared and positioned, and all other standard preoperational procedures are effectuated, exposure of the upper shaft of the femur is made in the usual manner. A small drill hole is made at the level of the lesser trochanter using a standard guide or template (not shown) and a thin guide wire or pin (not shown) is inserted through the cortex, across the fracture 11 and into the head 13. A template (not shown) compatible with the inventive compression hip screw 15 is placed over the guide wire (not shown) and clamped to the broken main portion of the femur 12 with an appropriate bone clamp (not shown). Utilizing holes in the template which coincide with holes 37 of barrel plate 17, two other holes (not shown) are drilled into the femur, across the fracture 11 and into the femoral head 13 substantially parallel to the center guide hole (not shown). Appropriately sized pins (not shown) are placed in the two additional holes so as to immobilize the femoral head 13 and prevent rotation thereof while the hole (not shown) for lag screw 16 is being prepared. The center guide wire (not shown) may now be removed. An appropriate two-step drill or reamer (not shown) may be used to drill the hole (not shown) for lag screw 16. An opening for threads 21 is not required because of the self-tapping provision of threads 21. Still using the template (not shown), a hole is drilled for the barrel 27 of barrel plate 17. If it is deemed desirable by the operating surgeon, holes may be drilled for the portion of pins 43 of pin assembly 18 which extend beyond the end 45 of barrel 27. If drilled, these holes should be slightly smaller than the size of pins 43 so as to effectuate a friction or force fit when pin assembly 18 is installed. Since the inner portion of the femur is soft, and readily penetrable by pins 43 with the application of a slight amount of force, the surgeon may decide not to drill such holes.

Figure 5:
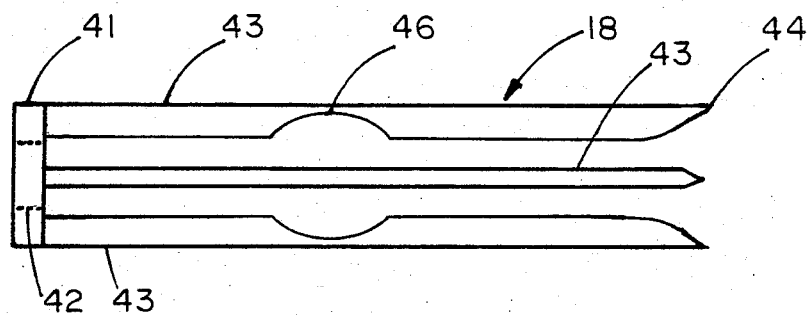
FIG. 5 is a side view of a pin assembly.
Figure 7:
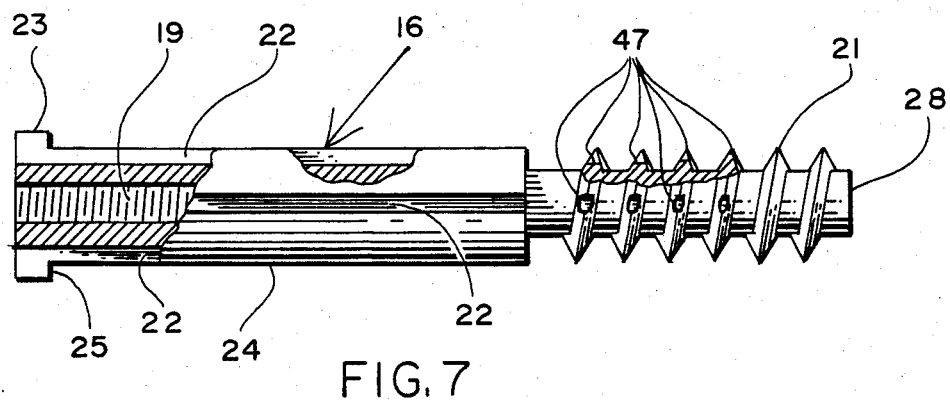
FIG. 7 is a side view of a lag screw, partially in cross section, illustrating apparatus for deflecting a pin associated therewith.

The template (not shown) may now be removed and the barrel plate 17 may be positioned using the wires (not shown) coinciding with holes 37 as a guide. With the barrel fully inserted in its opening and when the plate 30 is firmly positioned against the lateral side of the femur 10, the barrel plate 17 may be attached to the femur 10 using screws (not shown) inserted through holes 36. Lag screw 16 may now be inserted through bore 33 in barrel 27 and into the opening previously made by the aforementioned two-step drill or reamer. It is to be noted that there exists only a small amount of clearance space between bore 33 and shank portion 24 of lag screw 16 so as to provide a slip fit assembly arrangement between screw 16 and barrel 27. A turning tool (not shown), adapted to fit within the cutouts formed by grooves 22 in the head 23 of lag screw 16, may be used to rotationally turn and further insert lag screw 16 when lag screw 16 advances into the bone threads 21 cut corresponding threads in the femoral head 13. Rotation of lag screw 16 continues until bearing surface 25 of head 23 is firmly seated against bearing surface 26 in barrel 27 and the fractured parts of the femur are impacted. Lag screw 16 is then further rotated until the grooves 22 in lag screw 16 are in alignment with the grooves 35 in barrel 27. Pin assembly 18 is then inserted in the openings formed by grooves 22 and 35. Further insertion of pin assembly 18 (beyond the end of barrel 27) may be effectuated by the application of slight force such as by light tapping or pushing which drives the ends 44 of pins 43 into the bone beyond the end 45 of barrel 27 within grooves 22 of lag screw 16. The specially formed ends 44 of pins 43 may be tapered as shown in the drawings, i.e., they converge to a point above the axial centerline of the pins 43. In other words, the tip 44 of pins 43 slopes up and away from the axial centerline of pin assembly 18. These slopes attempt to cause the ends 44 of pins 43 to lift slightly out of groove 22 due to being driven into the bone. In order to so lift, pins 43 must slightly bend over their length between the end 45 of barrel 27 and ends 44. The amount of lifting, if any, is, of course, due to the relative stiffness of pins 43. Any lifting, however, enhances the net effect of pins 43 to positively prevent the femoral head 13 from rotating during the postoperative period because of the protrusion of the portion of pins 43 outside of grooves 22 as shown in FIG. 3. Pin lifting can be increased by increasing the flexibility of pins 43 by, for example, removing the portion shown by ramped line 46 in FIG. 5 and/or providing a ramped surface in grooves 22 as shown by ramped line 47 in FIG. 7.

Pin assembly 18 also serves to positively lock together lag screw 16 and barrel 27, and, therefore, barrel plate 17, so that lag screw 16 cannot rotate loose. The antirotational action of pins 43 and the lock between screw 16 and barrel 27 prevent any displacement of the femoral head following the surgery. Moreover, any continued impaction or reduction of the broken portions 12 and 13 of the femur 10 during the postoperative period is allowed by the inventive compression hip screw 15 because lag screw 16 can slide relative to barrel 27. Pins 43 prevent rotation of the femoral head 13 and lag screw 16 but allow sliding. Pin assembly 18 is prevented from being loosened from its assembled position as shown in FIG. 1 due to the friction or force fit between pins 43 and the bone.

Upon completion of the procedure outlined above, the completed operation may be checked by appropriate x-rays and the operative site is closed in a routine manner. It is to be noted that although the above-described installation procedure is not intended to be a complete detailed step-by-step procedure but merely generally illustrative of the manner in which the invention may be used, any description of the invention as to its features and functions are intended to form a part of this specification.

Figure 6:
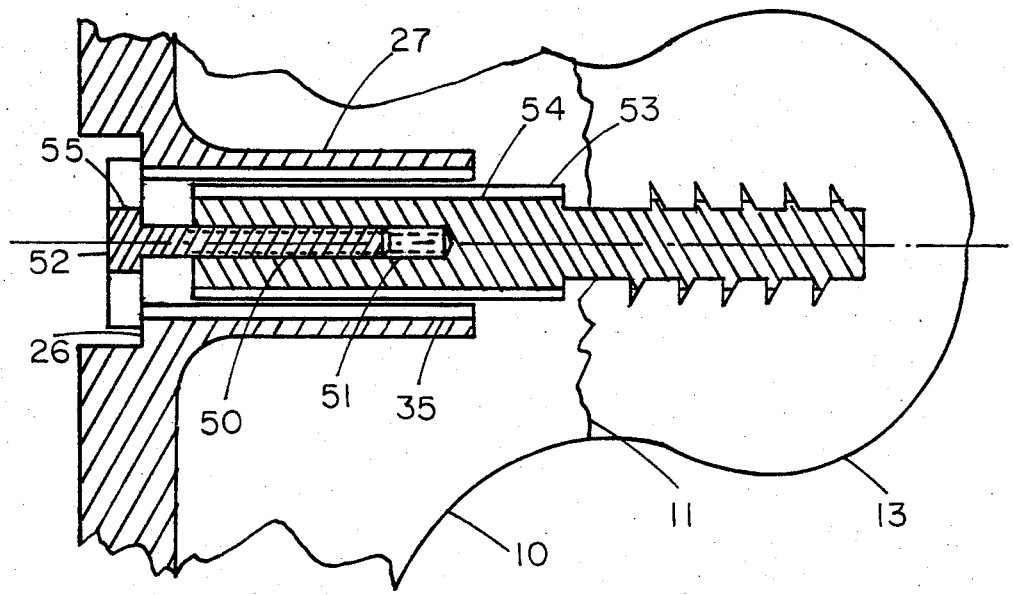
FIG. 6 is a partial, cross-sectional view of another embodiment of the present invention.

FIG. 6 illustrates another embodiment of the inventive compression hip screw 15. In this embodiment, a screw 50 is used to apply the compressive force to the broken components of the femur 10 in lieu of the head 23 of the lag screw 16 of the previous embodiment. Screw 50 threadingly engages with threads 51 of lag screw 53 which in this embodiment are right-handed threads. When head 52 of screw 50 contacts bearing surface 26 further rotation of screw 50 causes reduction of the fracture 11. Since threads 51 are being used for compression purposes, grooves 54 in lag screw 53 may be used for both inserting and withdrawing lag screw 53 by the use of a tool as previously described.

A pin assembly 18 is again used with the embodiment of FIG. 6 but is not shown for purposes of simplicity. Pin assembly 18, however, now fits within aligned grooves 35, 54 and 55 in barrel 27, lag screw 53 and screw 50, respectively.

While the invention has been described, disclosed, illustrated and shown in certain terms or certain embodiments or modifications which is has assumed in practice, the scope of the invention is not intended to be nor should it be deemed to be limited thereby and such other modifications or embodiments as may be suggested by the teachings herein are particularly reserved especially as they fall within the breadth and scope of the claims here appended.

I claim:

1. An implantable hip screw adapted for internal fixation and compression of a fractured portion of the proximal femur comprising plate and barrel means for attaching said hip screw to the lateral side of said femur, said plate and barrel means having a bore therethrough with said barrel being positioned wthin the femur, screw means comprising an elongated screw for internally fixing the fractured portion of said femur, said screw being slidingly received within said bore of said plate and barrel means and extending out of said barrel across the fracture line and into the fractured portion of said femur with the threads of said screw being located within the fractured portion, said screw including a head and said barrel includes a counterbore with said screw head being in bearing contact with a bearing surface created by said counterbore, compressing means for compressing said fractured portion ot said femur, said compressing means acting in conjunction with said screw means and said plate and barrel means, and means for preventing rotation of said fractured portion relative to said femur and for preventing rotation of said screw means within said plate and barrel means and for allowing axial sliding of said screw means relative to said plate and barrel means comprising one or more axial grooves in said bore of said barrel, one or more axial grooves in the surface of said screw, said grooves in said barrel and said screw being aligned with each other and an elongated rod positioned within each of said one or more aligned grooves.

2. The apparatus of claim 1, wherein said screw head in bearing contact with said bearing surface comprises the means for compressing said fractured portion to said femur.

3. An implantable hip screw adapted for internal fixation and compression of a fractured portion of the proximal femur comprising plate and barrel means for attaching said prosthesis to the lateral side of said femur, said plate and barrel means having a bore therethrough, screw means comprising an elongated screw for internally fixing the fractured portion of said femur, said screw means being slidingly received within said bore of said plate and barrel means and extending out of said barrel across the fracture line and into the fractured portion of said femur with the threads of said screw being located within the fractured portion, compressing means for compressing said fractured portion to said femur, said compressing means acting in conjunction with said screw means and said plate and barrel means, and means for preventing rotation of said fractured portion relative to said femur and for preventing rotation of said screw means within said plate and barrel means and for allowing axial sliding of said screw means relative to said plate and barrel means comprising one or more axial grooves in said bore of said barrel, one or more axial grooves in the surface of said screw, said grooves in said barrel and said screw being aligned with each other and an elongated rod positioned within each of said one or more aligned grooves, said rods being positioned within said barrel and extending out of said barrel within said one or more grooves in said screw and into the fractured portion of said femur, said rods protruding above the major diameter of the threads in said screw wherein said one or more grooves in said elongated screw includes ramping means at the location of the threads in the fractured portion of said femur whereby said elongated rod positioned therein is caused to extend further out of said groove and further into the fractured portion of said femur.

4. The apparatus of claim 3 wherein said elongated rod includes a reduced thickness section to allow the elongated rod to be more easily flexed.

* * * * *